(12) United States Patent
Lei et al.

(10) Patent No.: US 11,866,707 B2
(45) Date of Patent: Jan. 9, 2024

(54) USE OF NON-CODING RNA SNHG17 AS BIOMARKER AND THERAPEUTIC TARGET

(71) Applicant: ZHEJIANG CANCER HOSPITAL, Hangzhou (CN)

(72) Inventors: Lei Lei, Hangzhou (CN); Xiaojia Wang, Hangzhou (CN)

(73) Assignee: ZHEJIANG CANCER HOSPITAL, Hangzhou (CN)

( * ) Notice: Subject to any disclaimer, the term of this patent is extended or adjusted under 35 U.S.C. 154(b) by 0 days.

(21) Appl. No.: 18/048,451

(22) Filed: Oct. 21, 2022

(65) Prior Publication Data

US 2023/0374516 A1    Nov. 23, 2023

Related U.S. Application Data

(63) Continuation of application No. PCT/CN2022/115048, filed on Aug. 26, 2022.

(30) Foreign Application Priority Data

May 18, 2022   (CN) .......................... 202210537260.7

(51) Int. Cl.
   *C12N 15/113*   (2010.01)
   *A61P 43/00*    (2006.01)
(52) U.S. Cl.
   CPC .......... *C12N 15/1135* (2013.01); *A61P 43/00* (2018.01); *C12N 2310/122* (2013.01)

(58) Field of Classification Search
   CPC .......... C12N 15/1135; C12N 2310/122; A61P 43/00
   See application file for complete search history.

(56) References Cited

U.S. PATENT DOCUMENTS

| 2021/0079474 A1 | 3/2021 | Mellios |
| 2021/0269881 A1 | 9/2021 | Moussaoui et al. |
| 2022/0081685 A1 | 3/2022 | Salathia et al. |

FOREIGN PATENT DOCUMENTS

| CN | 101237884 A | 8/2008 |
| CN | 102448450 A | 5/2012 |
| CN | 114652736 A | 6/2022 |

*Primary Examiner* — J. E. Angell
(74) *Attorney, Agent, or Firm* — True Shepherd LLC; Andrew C. Cheng

(57) ABSTRACT

This invention discloses the use of non-coding RNA SNHG17 as a biomarker and a therapeutic target that relates to the technical field of tumor biotherapy. This invention discloses a use of the non-coding RNA SNHG17 for the manufacture of a detection agent for predicting the drug resistance of fulvestrant. This invention also discloses the use of shRNA for inhibiting non-coding RNA SNHG17 expression. This shRNA can knockdown the expression of the non-coding RNA SNHG17 efficiently. In this way, the sensitivity of fulvestrant-resistant breast cancer cells can be increased. So this invention has good prospects for drug development.

2 Claims, 12 Drawing Sheets

Specification includes a Sequence Listing.

USE OF NON-CODING RNA SNHG17 AS BIOMARKER AND THERAPEUTIC TARGET

CROSS-REFERENCE TO RELATED APPLICATIONS

This application is a continuation of International Patent Application No. PCT/CN2022/115048 with a filing date of Aug. 26, 2022, designating the United States, now pending, and further claims priority to Chinese Patent Application No. 202210537260.7 with a filing date of May 18, 2022. The content of the aforementioned applications, including any intervening amendments thereto, are incorporated herein by reference.

CROSS-REFERENCE TO A SEQUENCE LISTING

This application includes a Sequence Listing submitted electronically as an xml file named SEQ_list.xml, created on Aug. 16, 2022, with a size of 12,684 bytes. The Sequence Listing is incorporated by reference herein.

TECHNICAL FIELD

The present invention relates to the technical field of tumor biotherapy, and in particular, to the field of use of non-coding RNA SNHG17 as a biomarker and a therapeutic target.

BACKGROUND OF THE PRESENT INVENTION

Breast cancer is a female malignant tumor with the highest incidence rate in the global scope today. The morbidity each year is about 30.4 million and the morbidity presents a continuously rising trend. Female health is seriously affected by breast cancer. In addition, nearly 70% of breast cancer is a hormone receptor-positive breast cancer, so the treatment method and the medicine based on the hormone receptor-positive breast cancer are critical. Endocrine therapy is a common method for treating such breast cancer in the prior art. Although it is an effective treatment method in the prior art, there is still a large defect, that is, primary or secondary endocrine resistance in endocrine therapy. That may seriously affect the treatment effect of patients so that the therapeutic effect unable to achieve the expected results. Currently, there is no effective biomarker that can be used to predict the sensitivity of fulvestrant or for targeted therapy of reverse drug resistance.

In recent years, the effect of epigenetic regulation mechanisms taking non-coding RNA as a core in life activities is increasingly important. Long non-coding RNA is a non-coding RNA molecule with a transcript length of 200 nt or more and is generally considered to have a protein-coding function. However, more and more studies show that the expression of long non-coding RNA has high specificity in different tissues, not only the expression level is closely related to different stages of tumor development and different histological types of tumor development, but also closely related to regulatory function in tumorigenesis and tumor progression. So long non-coding RNA can be used as a specific marker for tumor detection and as a tumor treatment target.

SUMMARY OF PRESENT INVENTION

The present disclosure proposes a use of non-coding RNA SNHG17 as a biomarker and a therapeutic target. By detecting the expression of the non-coding RNA SNHG17 in breast cancer, it is possible to predict fulvestrant resistance; and the sensitivity of the drug-resistant breast cancer cells to fulvestrant can be improved by knockdown of the expression of the non-coding RNA SNHG17.

The use of shRNA for inhibiting non-coding RNA SNHG17 expression in manufacture of a medicament for reversing drug resistance of fulvestrant. The coding sequences of the shRNA are represented by SEQ ID NO. 1 and SEQ ID NO. 2, or represented by SEQ ID NO. 3 and SEQ ID NO. 4.

The use of a construct in manufacture of a medicament for increasing drug sensitivity of breast cancer cells to fulvestrant, the construct is made by inserting the shRNA according to claim 1 into a lentiviral vector plasmid pLKO.1-GFP-Puro.

In some embodiments, the constructs are stored in the form of lyophilization preparations.

The use of non-coding RNA SNHG17 in manufacture of a detection agent for predicting drug resistance of fulvestrant.

In some embodiments, the detection agent comprises primers for detecting the expression of the non-coding RNA SNHG17.

In some embodiments, the primers are represented by SEQ ID NO. 5 and SEQ ID NO. 6.

The use of shRNA of inhibiting non-coding RNA SNHG17 expression and fulvestrant for the manufacture of a medicament for breast cancer treatment, wherein the coding sequences of the shRNA are represented by SEQ ID NO. 1 and SEQ ID NO. 2, or represented by SEQ ID NO. 3 and SEQ ID NO. 4.

A pharmaceutical composition, comprising fulvestrant, the above-mentioned shRNA or the above-mentioned construct, and a pharmaceutically acceptable carrier and/or excipient.

In some embodiments, the constructs are stored in the form of lyophilization preparations.

This disclosure is based on the abnormal expression of the non-coding RNA SNHG17 in different breast cancer tissues. Detecting the non-coding RNA SNHG17 in breast cancer cell samples can help determine whether the breast cancer cells are fulvestrant-resistant. That helps to develop a more effective treatment, and the treatment effect can be improved. In addition, this disclosure also provides shRNA for non-coding RNA SNHG17 knockdown; and by knocking down the expression of non-coding RNA SNHG17, the reversal of the fulvestrant resistance of breast cancer can be achieved. So the sensitivity of the drug-resistant breast cancer cells to fulvestrant can be improved, and the treatment effect is improved.

DETAILED DESCRIPTION OF PREFERRED EMBODIMENTS

Figure 1:
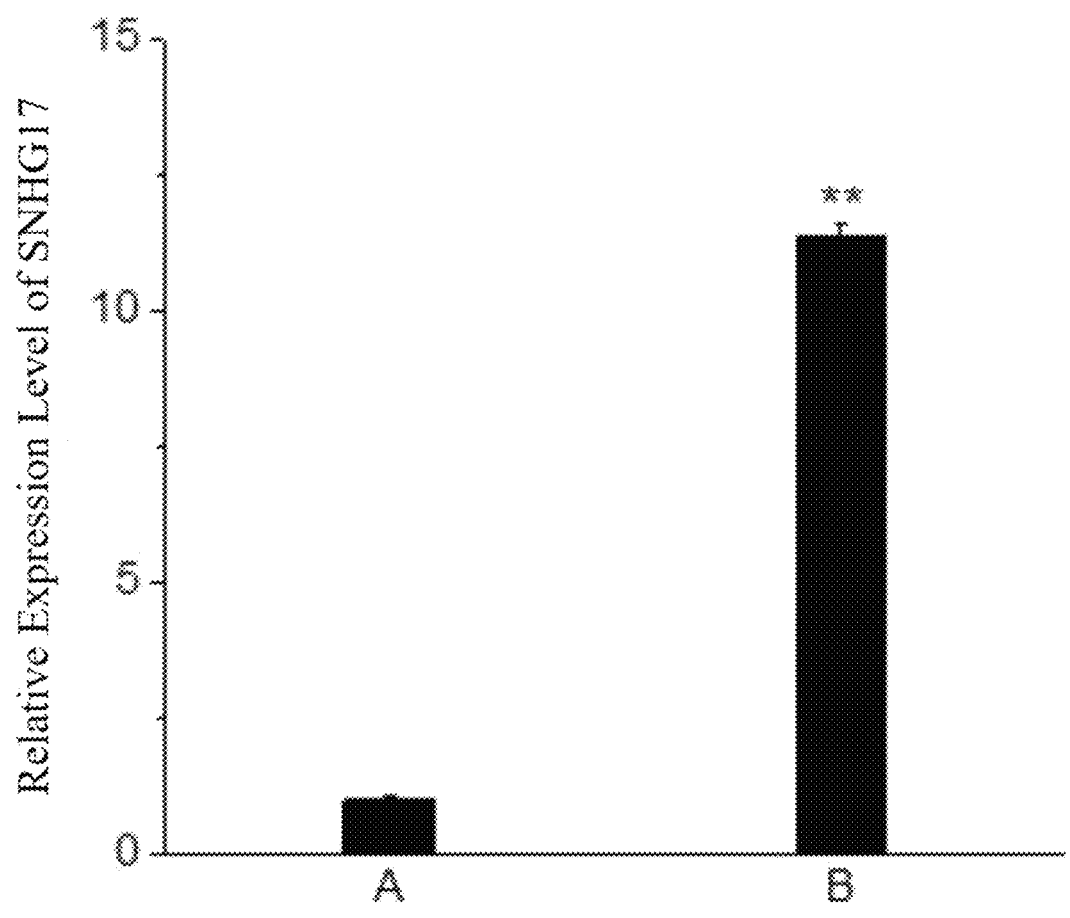
FIG. 1 is a relative expression level of SNHG17 in MCF-7 and MCF-7R cells according to Embodiment 1.

It should be noted that the following detailed description is exemplary and intended to provide further explanation of the invention. Unless otherwise defined, all technical and scientific terms used herein have the same meaning as commonly understood by skilled in the art to which this invention belongs.

It should be noted that the terminology used herein is for the purpose of describing particular embodiments only and is not intended to limit the embodiments according to the disclosure. As used herein, the singular forms are intended to include the plural forms as well, unless the context clearly indicates otherwise.

In order to enable those skilled in the art to understand the technical solutions of the disclosure more clearly, the disclosure will be described in further detail below in conjunction with the embodiments.

Embodiments 1

1. The expression level of the long non-coding RNA SNHG17 in fulvestrant-sensitive breast cancer cell lines and fulvestrant-resistant breast cancer cell lines is detected. MCF-7 is a fulvestrant-sensitive breast cancer cell line; MCF-7R is a fulvestrant-resistant breast cancer cell line.

1.1 MCF-7 cells were obtained from the ATCC cell bank, the MCF-7 cells were cultured in DMEM complete medium containing 10 wt % fetal bovine serum, and 200 U/mL penicillin and 200 U/mL streptomycin were added to the culture medium.

1.2 Construction of MCF-7R cell line: inoculating 1×10^7 cells of MCF-7 cells with logarithmic growth phase for a plate of 10 cm (with DMEM complete medium containing 10 wt % fetal bovine serum, penicillin 200 U/mL, streptomycin 200 U/mL as a culture medium); adding 1 μmol/L fulvestrant into the culture medium after cell growth was stable; added an equal concentration of fulvestrant after changing the medium every 48 hours. After 12 months, diluted by limited dilution, then the monoclonal cell line (called MCF-7R) resistant to breast cancer MCF-7 fulvestrant was obtained by the method, and then expanded without drug intervention. In order to maintain the fulvestrant resistance of MCF-7R, it was cultured in a medium containing 0.5 μmol/L fulvestrant.

1.3 RT-PCR detection of SNHG17 expression levels in MCF-7 and MCF-7R cells 1.3.1 Total RNA was extracted by Trizol MCF-7 and MCF-7R cells were respectively taken into 1.5 mL centrifuge tubes. After washing twice with 2 mL PBS, 1 mL Trizol was added; then pipetted repeatedly for 20 times to ensure that all cells were lysed. Then sucked into 1.5 mL centrifuge tubes and placed at room temperature for 5 minutes to fully lyse the sample. After adding 0.2 mL of chloroform, shook vigorously for 10 s and then place at room temperature for 2 minutes. centrifuge at 12,000 g at 4° C. for 15 minutes, transferred the upper colorless aqueous phase to a new centrifuge tube; then added 0.5 mL of isopropanol, inverted and mixed, and placed on ice for 10 minutes. After centrifuging at 12,000 g for 10 minutes at 4° C., RNA precipitation at the bottom of the tube can be seen. Carefully remove the supernatant, and added 1 mL of 75V/V % ethanol (prepared with DEPC water); then inverted and mixed, and centrifuged at 7,500 g at 4° C. After 5 min, carefully removed the supernatant; added 20 of DEPC water to dissolve, quantify, and quality inspection by Nanodrop spectrophotometer, and stored at −80° C. until use.

1.3.2 Reverse transcription

2 μg of total RNA, 1 μl of random primers were added into a tube, and DEPC water was added to 12 μL; then the product was immediately placed on ice for 4 min after incubation at 68° C. for 5 min. 4 μL of Reaction Buffer Buffer, 2 μL of 10 nM dNTP Mix, 1 μL of Reverse Transcriptase, M-MLV-Reverse, and 1 μL of Ase Inhibitor were added. Then water bath at 42° C. for 60 min, and then placed in a water bath at 70° C. for 15 min. After that, placed immediately on ice and allowed to stand for 5 min to obtain cDNA templates, then stored cDNA templates at −20° C.

1.3.3 RT-PCR detection of SNHG17 expression levels

The primers for SNHG17 and β-acting are shown in Table 1.

TABLE 1

RT-PCR Primer Sequences

| | Type | Sequences |
|---|---|---|
| GADPH | upstream primer | 5'-TGTTGTGGATCTGACCTGCC-3' (SEQ ID NO. 8) |
| | downstream primer | 5'-AAGTCGCAGGAGACAACCTG-3' (SEQ ID NO. 9) |
| SNHG17 | upstream primer | 5'-TGCTTGTAAGGCAGGGTCTC-3' (SEQ ID NO. 5) |
| | downstream primer | 5'-ACAGCCACTGAAAGCATGTG-3' (SEQ ID NO. 6) |

Take 1 μL of cDNA from each group of cells as a template for PCR reaction (10 μL). PCR reactions are shown in Table 2.

TABLE 2

PCR Reactions (10 μL)

| cDNA template | 1 μL |
|---|---|
| 2 × SYBR Premix Ex Taq | 5 μL |
| upstream primer (10 μM) | 0.2 μL |
| downstream primer (10 μM) | 0.2 μL |
| ddH$_2$O | 3.6 μL |

The reaction conditions were: pre-denaturation at 95° C. for 3 min; denaturation at 95° C. for 15 s; annealing at 60° C. for 30 s; extension at 72° C. for 30 s; amplification for 40 cycles; and extension at 72° C. for 10 min. Using GAPDH as a reference gene, the relative expression level of SNHG17 was calculated by the $2^{-\Delta\Delta CT}$ method. The relative expression levels of SNHG17 in MCF-7 and MCF-7R cells are shown in FIG. 1, where A stands for MCF-7 parental cells, B stands for MCF-7R fulvestrant-resistant cells, **P<0.01 indicates the data had statistical significance.

It can be seen from FIG. 1 that the expression level of the long non-coding RNA SNHG17 in the MCF-7 parent cell is significantly lower than that of the MCF-7 R fulvestrant-resistant cell, which indicates that the expression level of the long non-coding RNA SNHG17 in the fulvestrant-resistant breast cancer cell lines is higher than that of the fulvestrant-sensitive breast cancer cell line.

1.4 Fluorescence in situ hybridization (FISH) experiment 1.4.1 MCF-7, MCF-7 R cells 1×10³ were inoculated on a 6-well plate, and cultured overnight at 37° C.; after being washed twice with 1×PBS, 1 mL of 4 g/mL of paraformaldehyde was added for fixation for 15 min. The suspension was applied to adherent slides, and a suspension of about 50 µl per slide was added; constant temperature drying at 60° C. for 10 min to obtain cell smears.

1.4.2 The probe sequence is 5'-AGTCTCC-CATGTCTGGACCCCGAATCTTG-3' (SEQ ID NO 0.7) and FITC (fluorescein isothiocyanate) fluorescent groups were added to the 5' end of the probe sequence as universal fluorescent labels of the FISH probe, and synthesized by Sangon Biotech (Shanghai) Co., Ltd.

1.4.3 Cell smears were taken as samples and the samples were digested with pepsin solution (10 V/V % pepsin water solution 100 mL+pure water 40 mL+1 mol/L hydrochloric acid 400 µL) at 37° C. for 10 minutes, then dehydrated in a gradient ethanol solution of 70 V/V %, 90 V/V %, 100 V/V % for 1 min, and air-dried; the fluorescent labeling probe 10 µL is dropwise added to the samples in a darkroom, the fluorescence concentration was 10 ng/µL; the samples were covered by coverslips and placed in a preheated FISH dedicated wet box; denaturation was performed at 90° C. for 10 min, and the wet box with samples was placed in an incubator at 37° C. for 4 h; the smears were soaked in 2×SSC for 2 min in the darkroom; after careful removal of the coverslips, samples were washed three times by 2×SSC for 3 minutes each time;

DAPI re-staining: dropwise adding DAPI 10 µl on samples in the darkroom, covering the samples with coverslips and placing in a cassette; incubating at 25° C. for 5 min then slowly removing the coverslips; using 2×SSC 3 times for 3 times each time, and then dehydration for 1 min in a gradient ethanol solution of 70 V/V %, 90 V/V %, 100 V/V %; dropwise added fluorescence quenching mounting medium and used laser confocal for inspection. Since the FITC fluorescent dye was green under green excitation light, the DAPI fluorescent dye was blue under the UV light, FITC channel and DAPI channel were selected in the photographing process for observing and taking photos.

Figure 2:
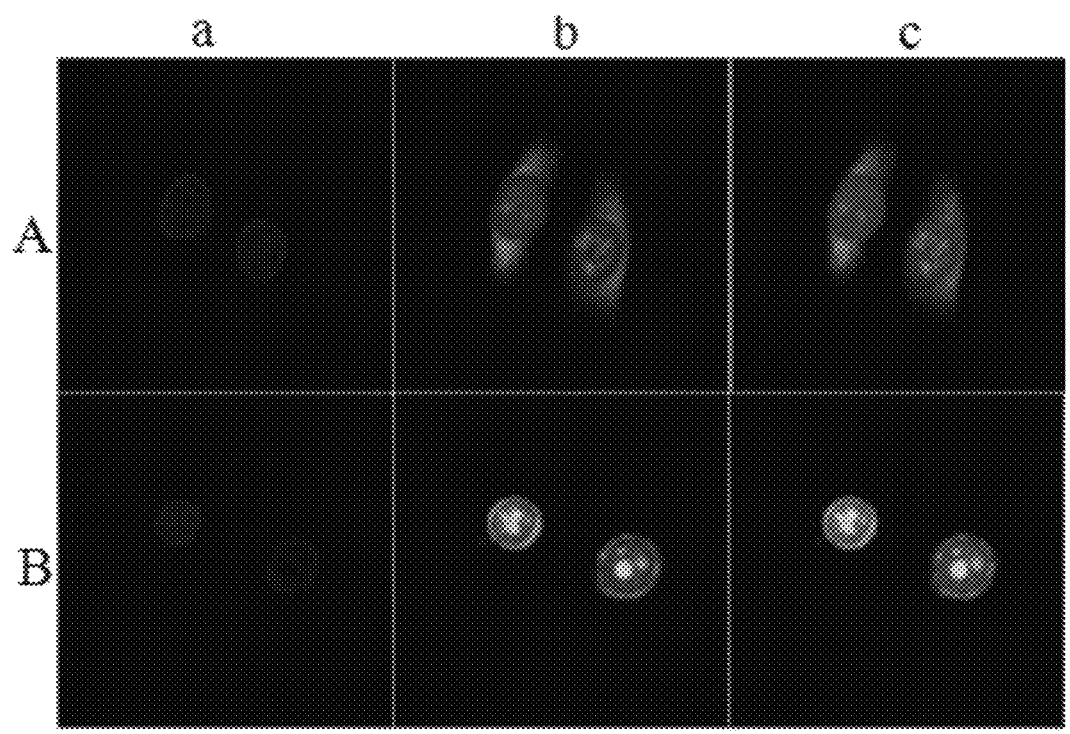
FIG. 2 is a fluorescence in-situ hybridization map of SNHG17 in cells according to Embodiment 1.

The fluorescence in situ hybridization of SNHG17 in cells is shown in FIG. 2, wherein A stands for MCF-7 parent cell, B stands for MCF-7R fulvestrant-resistant cell, a stands for a photograph with a DAPI channel, b stands for a photograph with FITC channel, and c stands for a photo with a hybrid channel.

It can be seen from FIG. 2 that the expression of SNHG17 in MCF-7R fulvestrant-resistant cells is higher than that in MCF-7 parental cells, that is, FISH experiments proved that the expression of SNHG17 is higher in fulvestrant-resistant cells than that in MCF-7 parental cells.

Embodiments 2

1. Construction of SNHG17-overexpression breast cancer cell line 1.1 Primers for amplifying SNHG17
upstream primer: 5'-AG-GAGCTAGCTGCTTGTAAGGCAGGGTCTC-3' (SEQ ID NO 0.10),
downstream primer: 5'-ATGCGAATTCACAGCCACT-GAAAGCATGTG-3' (SEQ ID NO 0.11);

The underlined parts of the upstream primer and downstream primer are Nhe 1 and EcoR 1 restriction enzyme site.

1.2 PCR amplification of human SNHG17 gene fragment

The total RNA of breast cancer cell MCF-7 was extracted by Trizol, and then reverse transcribed into cDNA (the method was the same as 1.3.1 and 1.3.2 in Embodiments 1). PCR reactions (total 20 µL) are shown in Table 3.

TABLE 3

| PCR Reactions | |
|---|---|
| TaKaRaLA Taq ® enzyme | 1 µL |
| upstream primer (10 µM) | 0.4 µL |
| downstream primer (10 µM) | 0.4 µL |
| cDNA template | 2.0 µL |
| ddH₂O | 12.2 µL |
| PCR buffer (5×) | 4 µL |

The reaction conditions were: pre-denaturation at 94° C. for 5 min; denaturation at 95° C. for 10 s; annealing at 62° C. for 30 s; extension at 72° C. for 60 s; amplification for 39 cycles; and extension at 72° C. for 10 min. The PCR products were gel electrophoresed and the target fragments were recovered.

1.3 The PCR products of SNHG17 and pcDNA3.1 plasmid were digested by double enzymes. The enzyme digestion reactions are shown in Table 4.

TABLE 4

| Enzyme Digestion Reactions | | |
|---|---|---|
| | products of SNHG17 | pcDNA3.1 plasmid |
| 10 × Buffer H | 5 µL | 5 µL |
| EcoR I | 2 µL | 2 µL |
| Nhe I | 2 µL | 2 µL |
| PCR products of SNHG17 | 41 µL | — |
| pcDNA3.1 plasmid | — | 5 µL |
| ddH₂O | — | 36 µL |

The reaction condition was 37° C. water bath for 60 min.

1.4 The enzymes digested pcDNA3.1 plasmid and SNHG17 PCR product were electrophoresed respectively and the target fragments were recovered. Then the digested pcDNA3.1 plasmid and SNHG17 PCR product were ligated. The ligation reactions are shown in Table 5.

TABLE 5

| Ligation Reactions | |
|---|---|
| digested products of SNHG17 | 6.5 µL |
| digested pcDNA3.1 plasmid | 2.5 µL |
| 10 × T4 DNA Ligase Buffer | 1.0 µL |
| T4 DNA Ligase | 0.5 µL |

The reaction condition was: 25° C. water bath for 60 min.

1.5 The plasmids with SNHG17 were transformed into *E. coli* DH5a. After being screened overnight by LB (with 100

µg/mL ampicillin) plate, the positive clones were picked up for expansion culture, and plasmids were extracted by using a plasmid extraction kit from E. coli DH5a for sequencing. The sequencing result verifies that the recombinant plasmids pcDNA3.1-SNHG17 were successfully constructed.

1.6 Cell transfection 1.6.1 MCF-7 breast cancer cells in a good growth state were inoculated in 24-well plates at $2 \times 10^5$ cells/well, and 500 µL of DMEM complete medium was added to each well to culture until the cell confluence reached 60%; then cell transfection was started.

1.6.2 1 µg of recombinant plasmid pcDNA3.1-SNHG17 was added into 50 µL of DMEM complete medium and mixed evenly to obtain system N1. 2.5 µL Lipofectamine 2000 was added into 50 µL DMEM complete medium, then mixed evenly and standing for 5 min; then system N2 was obtained. System N was obtained by mixing system N1 and system N2 evenly and standing for 25 min.

1.6.3 The original medium in the 24-well plates was discarded, and 400 µL DMEM complete medium and 100 µL system N were added to each well. After 6 hours, each well was replaced with 2 mL DMEM complete medium containing 10 wt % fetal bovine serum. DMEM complete medium with 600 µg/mL G418 (Geneticin) was used for screening cells for 14 days and the medium was changed every 3 days. Maintained G418 resistant culture when monoclonal cell lines were selected. Maintain the concentration of G418 at 300 µg/mL to obtain stably transfected SNHG17 cell lines. The selected cells were passaged in 96-well plates by limiting dilution. After cells were screened, monoclonal cell lines were made and amplified in DMEM complete medium containing 300 µg/mL G418. The experiment was divided into the control group (empty lentivirus) and pcDNA3.1-SNHG17 group and obtained SNHG17-overexpressing control breast cancer cell line and SNHG17-overexpressing breast cancer cell line. The relative expression level of SNHG17 in SNHG17-overexpressing breast cancer cells is shown in FIG. 3, where C stands for SNHG17-overexpressing control breast cancer cells, and B stands for SNHG17-overexpressing breast cancer cells. **P<0.01 indicates the data had statistical significance.

Figure 3:
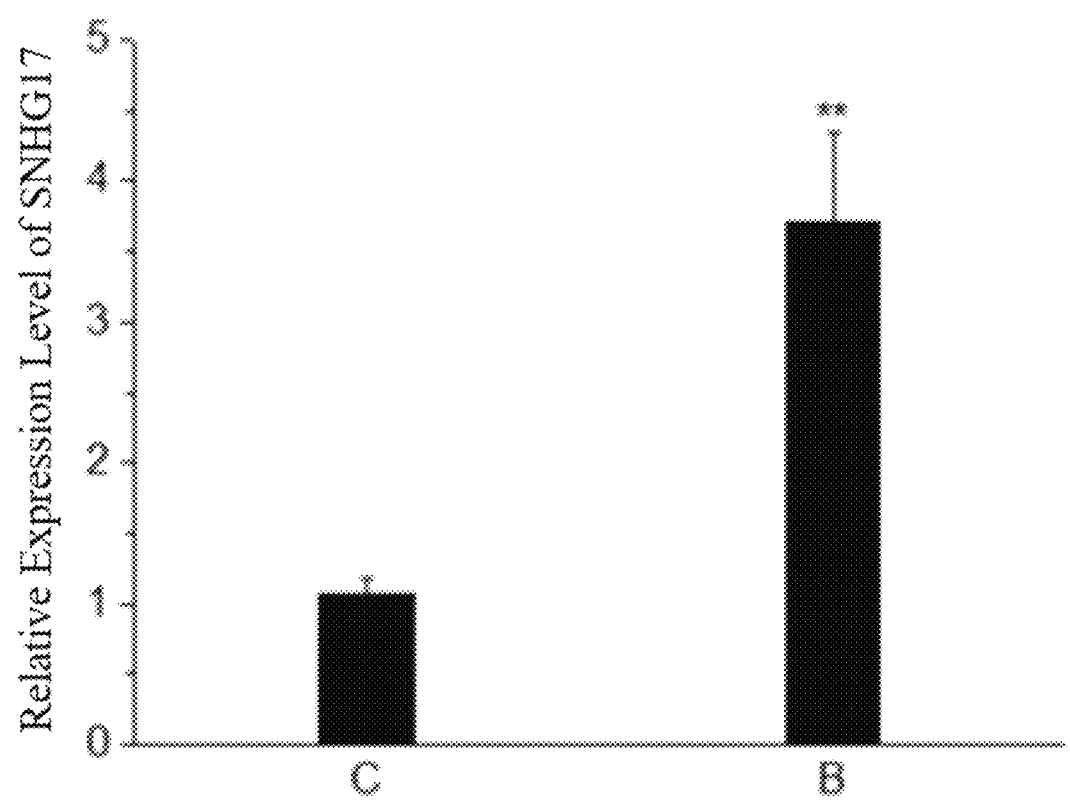
FIG. 3 is a relative expression level of SNHG17 overexpressed breast cancer cells according to Embodiment 2.

It can be seen from FIG. 3 that after MCF-7 breast cancer cells were transfected, the relative expression level of SNHG17 in SNHG17-overexpressing breast cancer cells was significantly higher than that in SNHG17-overexpressing control breast cancer cells.

2. Plate colony formation experiment

The above-mentioned SNHG17-overexpressing control breast cancer cells and SNHG17-overexpressing breast cancer cells were selected for experiments to detect the drug resistance to fulvestrant. 1000 well-grown cells were inoculated into a culture plate (diameter 60 mm) containing DMEM complete medium, then gently shook the culture plate to disperse the cells evenly. The cells were incubated at 37° C., 5V/V % $CO_2$ for 15 days, and replaced complete medium every 3 days. When colonies were visible to the naked eye in the culture dish, the culture was terminated and the culture medium was discarded. After that, the cells were carefully washed twice by PBS and dried. Methanol was used for anchor cells for 15 min, then the methanol was discarded and cells were air-dried. Cells were stained with Giemsa staining solution (purchased from Merck) for 10 min, then the staining solution was slowly washed away with running water, and cells were air-dried. Experiments were divided into blank group (SNHG17-overexpressing control breast cancer stable cells, medium containing 6 µmol/L DMSO), control group (SNHG17-overexpressing control breast cancer cells, medium containing 6 µmol/L fulvestrant), overexpression group (SNHG17-overexpressing breast cancer cells, medium containing 6 µmol/L fulvestrant) 3 groups. The colony formation of the cells is shown in FIG. 4, wherein O stands for the blank group, P stands for the control group, and Q stands for the overexpression group.

Figure 4:
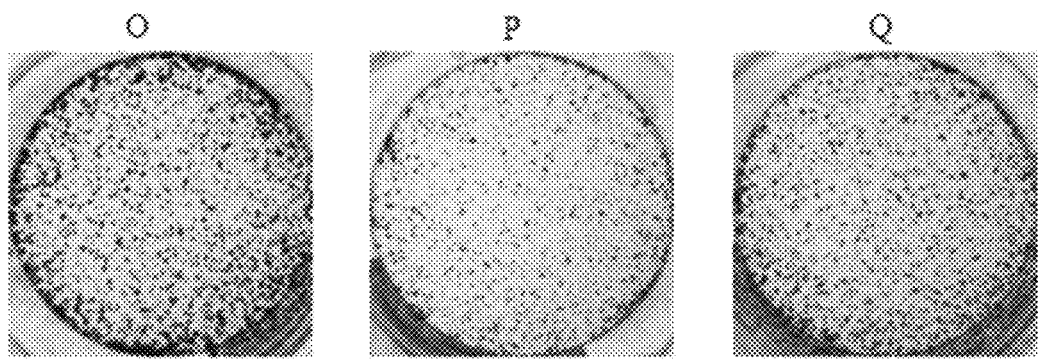
FIG. 4 is colonies of cells in Embodiment 2.

It can be seen from FIG. 4 that the number of colonies formed by SNHG17-overexpressing breast cancer cells is greater than that of SNHG17-overexpressing control breast cancer cells, which indicates that overexpression of SNHG17 in sensitive cell strains can enhance the resistance of breast cancer cells to fulvestrant.

3. Sensitivity detection of breast cancer cells to fulvestrant

MCF-7 and SNHG17 overexpressing breast cancer cells in the logarithmic growth phase were inoculated into 96-well plates (with DMEM complete medium) at a density of 3000 cells per well. Then cells were cultured in a 37° C. 5V/V % $CO_2$ incubator until the cells adhered to the plates. Then added fulvestrant respectively, and the final concentration was 0 (cell control group), 2, 4, 8, and 16 µmol/L. Each concentration was set in 4 duplicate wells, and a blank control group was set at the same time. After being cultured for 48 hours in a 37° C., 5V/V % $CO_2$ incubator, 20 µL of MTT (5 g/L) solution was added to each well. After culturing for 4 hours, discarded the medium and added triple solution (10 g SDS, 5 mL of isobutanol, 0.1 mL of 10M hydrochloric acid, and dd$H_2O$ to make a 100 mL solution) and incubated overnight. Then the absorbance (A570 nm) value was measured at 570 nm with an enzyme calibration. The triple solution was used as a blank control group to detect the cells' survival rate. Growth inhibition rate (%)= (control group $_{A570\ nm}$—experimental group $_{A570\ nm}$)/cell control group $_{A570\ nm} \times 100\%$. The growth inhibition rate of fulvestrant on breast cancer cells is shown in FIG. 5, wherein C stands for SNHG17-overexpressing control breast cancer cells, D stands for SNHG17-overexpressing breast cancer cells, *P<0.05, **P<0.01 indicates the data had statistical significance.

Figure 5:
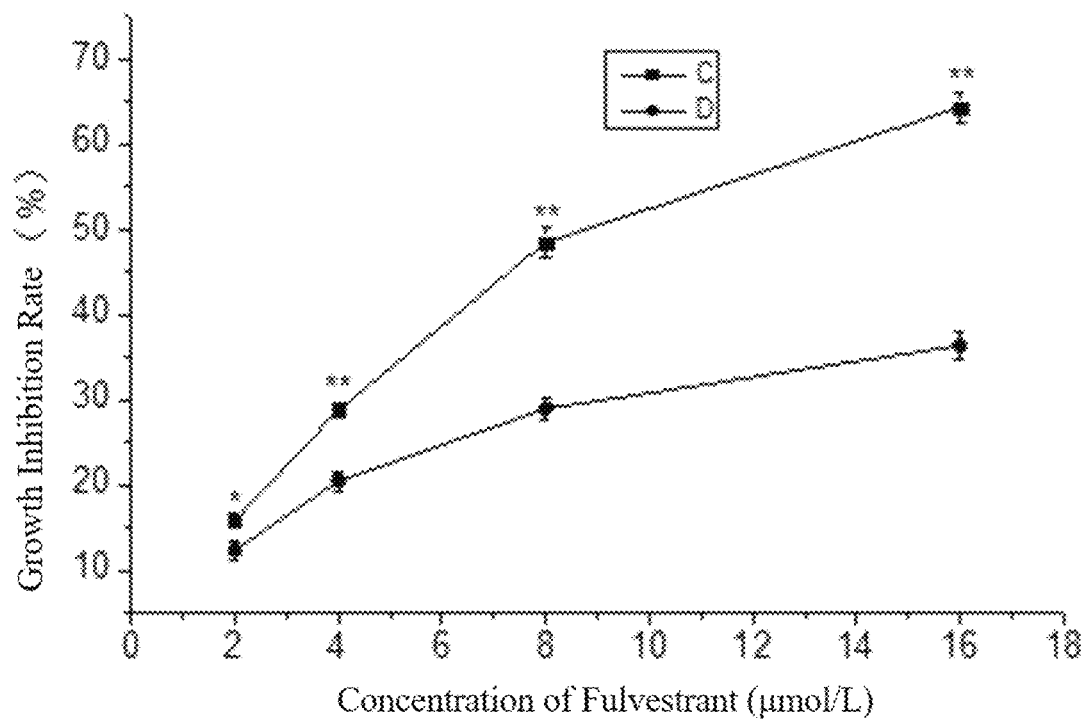
FIG. 5 is growth inhibition rate of fulvestrant on breast cancer cells according to Embodiment 2.

As can be seen from FIG. 5, the growth inhibition rate of fulvestrant on SNHG17-overexpressing breast cancer cells was significantly greater than that in SNHG17-overexpressing control breast cancer cells, which indicated that the overexpression of SNHG17 in sensitive cell strains would reduce breast cancer cells' sensitivity to fulvestrant.

Embodiments 3

1. 2 target sequences were designed based on the mRNA sequence of the human non-coding RNA SNHG17 gene (NR_015366.5). Target sequence 1 is GGATTGTCAGCTGACCTCTGT (SEQ ID NO 0.12) and target sequence 2 is GTGACGTGTCTTCAAGAAGAG (SEQ ID NO 0.13).

2. Construction of lentiviral interference vectors 2.1 PLKO.1-GFP-Pero (purchased from Shanghaiqiming Biotechnology CO., Ltd.) was selected as the lentiviral shRNA knockout plasmid vector.

2.2 shRNA was synthesized for each target sequence. The designed shRNA oligonucleotide chains (Table 6) were synthesized by Sangon Biotech (Shanghai) Co., Ltd.

TABLE 6 shRNA Oligonucleotide Sequences

| shRNA 1 | sense strand | 5'-CCGGTGGATTGTCAGCTGACCTCTGTTT CAAGAGAACAGAGGTCAGCTGACAATCCTTT TTTG-3' (SEQ ID NO. 1) |
|---|---|---|
| | antisense strand | 5'-AATTCAAAAAAGGATTGTCAGCTGACCT CTGTTCTCTTGAAACAGAGGTCAGCTGACAA TCCA-3' (SEQ ID NO. 2) |
| shRNA 2 | sense strand | 5'-CCGGTGTGACGTGTCTTCAAGAAGAGTT CAAGAGACTCTTCTTGAAGACACGTCACTTT TTTG-3' (SEQ ID NO. 3) |
| | antisense strand | 5'-AATTCAAAAAAGTGACGTGTCTTCAAGA AGAGTCTCTTGAACTCTTCTTGAAGACACGT CACA-3' (SEQ ID NO. 4) |

2.3 The PLKO.1-GFP-Puro vectors were extracted by a plasmid extraction kit, and the double enzyme digestion system was used for digesting: 1 μL EcoR 1, 1 μL Age 1, 5 μL, 10×NEB Cutsmart Buffer, 1 μg PLKO.1-GFP-Puro, ddH$_2$O (supplemented to 50 μL). Then PLKO.1-GFP-Puro vectors were incubated at 37° C. for 1 h. After that, the double-digested vector was recovered by agarose gel electrophoresis.

2.4 Dissolve the shRNA primers to a concentration of 100 μM with TE solution pH adjusted to 8.0, and then take the two corresponding strands for annealing. The annealing reactions are shown in table 7.

TABLE 7

Annealing Reactions

| ddH$_2$O | 35 μL |
|---|---|
| 10 × shRNA annealing buffer | 5 μL |
| shRNA sense strand | 5 μL |
| shRNA antisense strand | 5 μL |

The reaction conditions were: 95° C. for 5 min; then incubated at 85° C. for 5 min; 75° C. for 5 min; 70° C. for 5 min; then saved at 4° C. The end products were a 10 μM shRNA1 template and a 10 μM shRNA2 template, respectively.

2.5 Connect the shRNA to the plasmids, and the ligation reactions are shown in Table 8.

TABLE 8

Ligation Reactions

| shRNA template | 2 μL |
|---|---|
| digested PLKO.1-GFP-Puro victor | 2 μL |
| T4 DNA Ligase (10 U/mL) | 1 μL |
| 10 × T4 Buffer | 1 μL |
| ddH$_2$O | 4 μL |

After mixing the ligation reactions, centrifuged briefly and incubated at 22° C. for 2 h.

The ligation products were transformed into *E. coli* DH5a, and after overnight screening on LB (with 100 μg/mL ampicillin) plates, positive clones were picked for expansion culture. After that, the plasmids in *E. coli* were extracted using a plasmid extraction kit for sequencing. Sequencing results verified that the recombinant plasmids were successfully constructed. That is, the recombinant plasmids PLKO.1-shRNA1 and PLKO.1-shRNA2 for targeted silencing of the SNHG17 gene were constructed.

2.6 Lentivirus packaging

When 293FT cells were cultured in a 6 cm culture plate (with DMEM complete medium) to 70% confluence, the medium was replaced with DMEM complete medium; 2 μg recombinant plasmid PLKO.1-shRNA, 2 μg envelope vector psPAX2 (purchased from shanghaiqiming Biotechnology Co., Ltd.) and 2 μg of packaging vector pMD2.G (purchased from Shanghaiqiming Biotechnology Co., Ltd.) were dissolved in 300 μL of DMEM complete medium and mixed to obtain system X1, and added 18 μL of Lipofectamine 2000 transfection reagent (purchased from Thermo Fisher Scientific) in 300 μL DMEM complete medium and mix well to obtain system X2; then system X2 was added to system X1 and mix well. After standing for 10 min, it was added to the culture dish of 293FT cells, shaken gently, and incubated overnight at 37° C., 5V/V % CO$_2$. After 18 h, replaced the medium with 5 mL of DMEM complete medium containing 10 wt % fetal bovine serum, collected the supernatant (virus stock) after 48 h, and centrifuged the virus stock solution at 2500 rpm for 15 minutes. After centrifuging, the supernatant was filtered with a 0.45 μm filter, and the filtrate was stored at −80° C. The filtrate contained pLKO.1-shRNA lentivirus. According to the above method, empty lentivirus, pLKO.1-shRNA1 lentivirus and pLKO.1-shRNA2 lentivirus were obtained respectively.

2.7 MCF-7 cells in a good growth state were inoculated into 24-well plates, 4×10$^5$ cells per well, and 400 μL of DMEM complete medium containing 10 wt % fetal bovine serum was added to each well. After culturing at 37° C. in a 5V/V % CO$_2$ incubator for 24 h, the medium in the 24-well plate was removed. 500 μL of DMEM complete medium containing 10V/V % virus solution, 5 μg/mL polybrene, and 10 wt % fetal bovine serum was added. Then continue to culture for 48 h and detected the knockdown effect. The experiment was divided into the control group (empty lentivirus), pLKO.1-shRNA1 group, and pLKO.1-shRNA2 group. Detection of knockdown effect: The lentiviral vector carries green fluorescent protein, and the green fluorescence was observed with a fluorescence microscope after cells were infected by the virus for 96 hours; in this way virus infection of target cells can be observed. BD influx cell sorter is used for sorting knockdown cells and cells with GFP were obtained.

2.8 The control cells, pLKO.1-shRNA1 silenced cells, and pLKO.1-shRNA2 silenced cells were inoculated in 24-well plates at 4×10$^5$ cells per well. When cells were cultured until the confluence of the cells reached 85%, the expression of SNHG17 gene in each group of cells was detected by RT-PCR. The relative expression level of SNHG17 in the cells is shown in FIG. 6, where E stands for the control group (the control cells were silenced by empty lentivirus), and F stands for the pLKO.1-shRNA1 silenced cells, and G stands for the pLKO.1-shRNA2 silenced cell. * indicates the data compared with control group **P<0.01 indicates the data had statistical significance.

Figure 6:
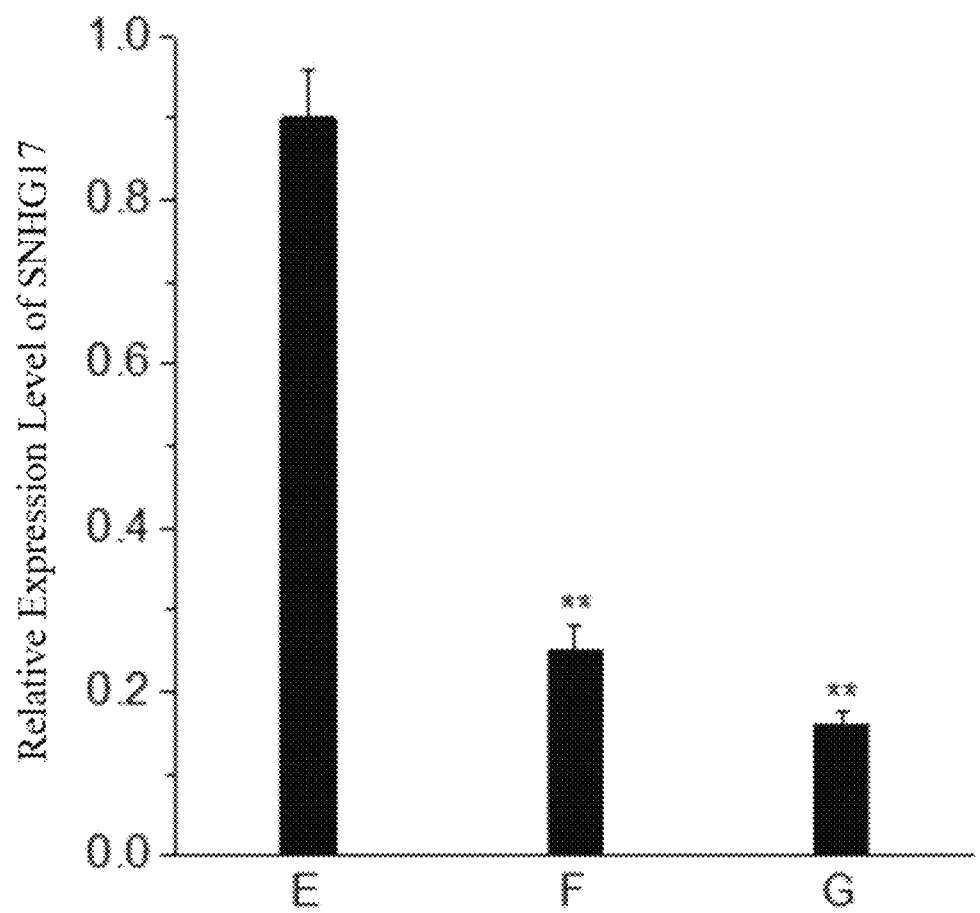
FIG. 6 is a relative expression level of SNHG17 in cells according to Embodiment 3.

As can be seen from FIG. 6, the relative expression level of SNHG17 in pLKO.1-shRNA1 silenced cells and pLKO.1-shRNA2 silenced cells were significantly lower than that in the control cells, which indicates that the pLKO.1-shRNA1 lentivirus and pLKO.1-shRNA2 lentivirus can significantly knock down the expression of SNHG17 gene.

3. Plate colony formation experiment

Control cells and pLKO.1-shRNA2 silenced cells were used for detecting fulvestrant resistance. 1000 well-grown cells were inoculated into a culture plate (diameter 60 mm) containing DMEM complete medium. Gently shook the culture dish in a cross direction to disperse the cells evenly and then cells were incubated at 37° C., 5V/V % $CO_2$ for 15 days. The complete medium was replaced every 3 days. When colonies were visible to the naked eye on the plate, the culture was terminated and the culture medium was discarded. Cells were washed twice with PBS, and then air-dried. Methanol was used for fixing cells for 15 min; then the methanol was discarded and cells were air-dried. After that, the cells were stained with Giemsa staining solution (purchased from Merck) for 10 min, and the staining solution was slowly washed away with running water. The experiment was divided into blank group (control cells with empty lentivirus+medium containing 6 μmol/L DMSO), control group (control cells with empty lentivirus+medium containing 6 μmol/L fulvestrant), Knockout group (pLKO.1-shRNA2 silenced cells+medium containing 6 μmol/L fulvestrant). The colony formation of cells is shown in FIG. 7, wherein R stands for the blank group, S stands for the control group, and T stands for the knockout group.

Figure 7:
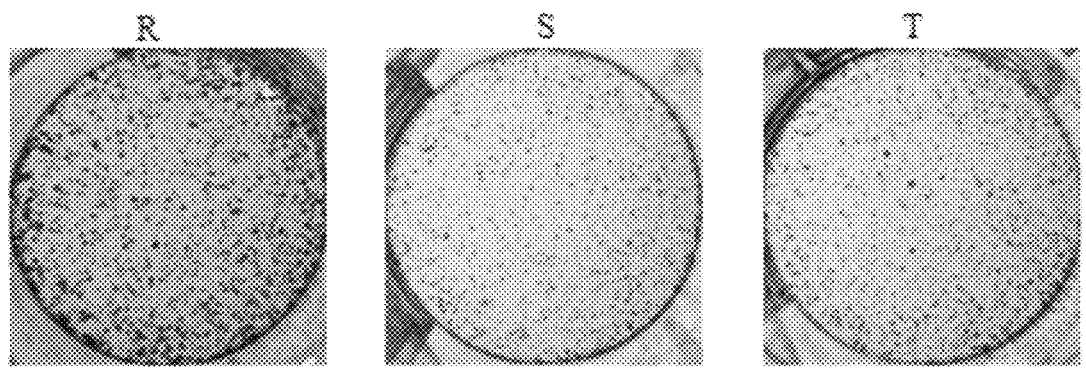
FIG. 7 is colonies of cells according to Embodiment 3.

It can be seen from FIG. 7 that the number of colonies in the knockout group is significantly smaller than that in the control group, which indicates that knockdown of SNHG17 can improve the sensitivity of breast cancer cells to fulvestrant.

Embodiments 4

1. Preparation of lyophilization lentiviral vector preparations

The lentiviral vector filtrate was prepared according to the preparation method of Embodiments 1 and concentrated at a rate of 1:50 by ultrafiltration to obtain a lentiviral vector concentrate. The titer of the lentiviral vector concentrate was $4.13 \times 10^7$ TU/mL.

Preparation of Lyophilization lentiviral vector protective agent solution: the pH value of the mixed solution was adjusted to 7.4 with 1 mol/L PB. The prepared Lyophilization lentiviral vector protective agent solution was added to the concentrate according to the volume ratio of Lyophilization lentiviral vector protective agent solution: lentiviral vector concentrate to 3:2, and mixed them evenly. Then lyophilization was operated. The lyophilization procedure was as follows: −60° C. for 3 h; −40° C. for 25 h, vacuum degree 1 Pa; −20° C. 10 h, vacuum degree 1 Pa; 0° C. 30 h, vacuum degree 1 Pa. The experiment was divided into 5 groups: K1 group, K2 group, K3 group, K4 group, and control group, with 6 repetitions in each group. The preparation method of the Lyophilization lentiviral vector protective agent in the K1 group was as follows: adding 15 wt % trehalose, 0.009 wt % L-alanine, 0.016 wt % histidine, 0.001 wt % $CaCl_2$, 0.0008 wt % $MgSO_4$ to the PBS. The preparation method of the Lyophilization lentiviral vector protective agent in the K2 group was as follows: adding 15 wt % trehalose, 1 wt % diacetin, 0.2 wt % glycerophosphorylcholine, 0.009 wt % L-alanine, 0.016 wt % histidine, 0.001 wt % $CaCl_2$, 0.0008 wt % $MgSO_4$. The preparation method of the Lyophilization lentiviral vector protective agent in the K3 group was as follows: adding 15 wt % trehalose, 1 wt % diacetin, 0.009 wt % L-alanine, 0.016 wt % Histidine, 0.001 wt % $CaCl_2$, 0.0008 wt % $MgSO_4$ to PBS. The preparation method of the Lyophilization lentiviral vector protective agent in the K4 group was as follows: adding 15 wt % trehalose, 0.2 wt % glycerophosphorylcholine, 0.009 wt % L-propane, 0.016 wt % histidine, 0.001 wt % $CaCl_2$), 0.0008 wt % $MgSO_4$ to PBS. The Lyophilization lentiviral vector protective agent of the control group was PBS.

2. Detection of bio-titer of lentivirus vectors

Take a 24-well plate as an example: 400 μL of 293FT cell suspension was added to each well, and the cell density was $1.0 \times 10^5$ cells/mL. 500 μL of bacterial endotoxin was added to lyophilization lentiviral vectors preparation and lyophilization lentiviral vectors preparation was reconstituted by water. After the dissolution was complete, DMEM was added to complete the solution for diluting The solution was serially diluted by 10 times, 100 times, and 1000 times. After diluting, 200 μL of lentiviral vector dilution was added to each well, and the well plate was placed in the incubator for 24 hours. The next day, the cells were supplemented with medium and cultured for 48 hours. After that, the 24-well lentiviral titer detection cell plate was taken out, cells were digested with trypsin; then the cells in each well were collected and transferred to a 1.5 mL centrifuge tube. After centrifuging for 5 min at 4° C., 1500 rpm, the cell precipitation was collected and the supernatant was discarded. 1 mL of pre-cooled PBS per tube was used to resuspend the cell precipitation; then it was centrifuged at 4° C., 1500 rpm for 5 min. After that, cell precipitation was washed twice by using PBS and then the PBS in the centrifuge tube was discarded. Then the cell precipitation was resuspended with 500 μl of pre-cooled PBS, and it was transferred to a flow tube. Flow cytometry on the machine to detect GFP-positive cells, collect data, and analyze the results. The method for detecting lentivirus titer by flow cytometry was as follows: select groups with a positive rate between 1 and 20% for titer calculation; the titer calculation formula is as follows:

Titer (TU/mL)=$DF \times N \times P N$;

N is the number of cells before lentivirus infection; P is the positive rate of cells (1-20%); V is the volume of lentivirus infection per well of cells; DF is dilution multiple, diluted 10 times means $DF=10^{-1}$; diluted 100 times means $DF=10^{-2}$; diluted 1000 times means $DF=10^{-3}$; TU is infection titer.

Figure 8:
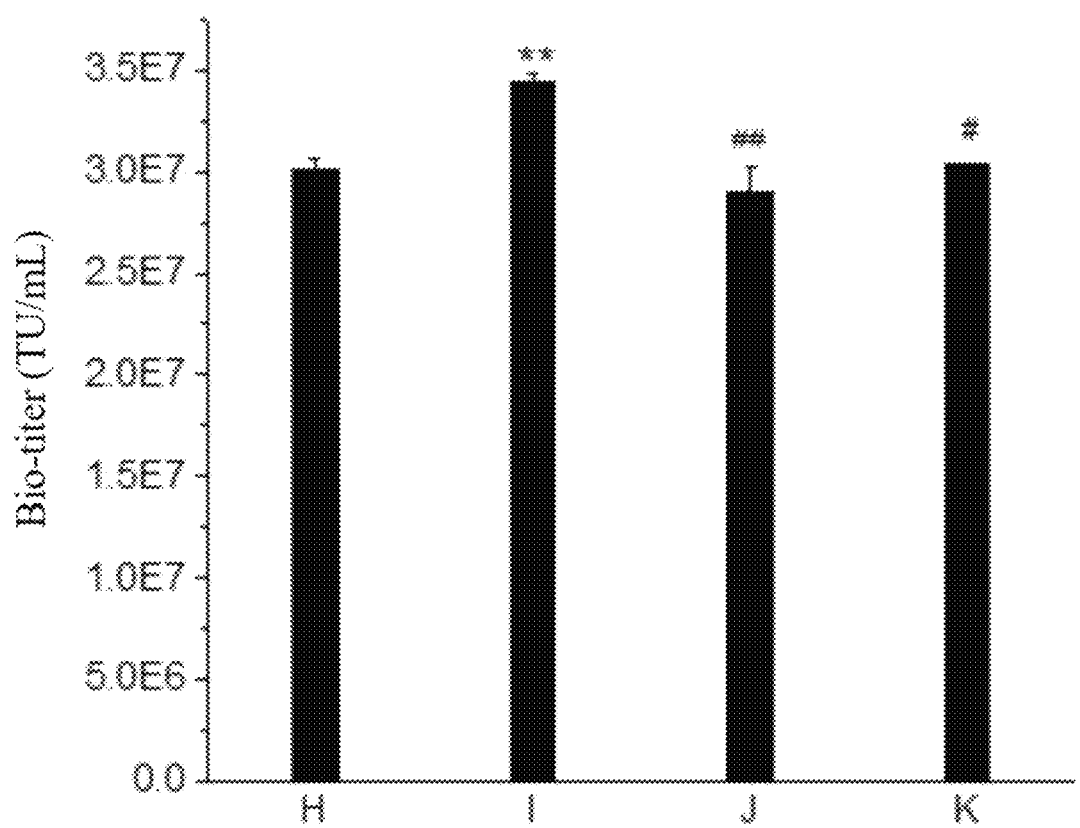
FIG. 8 is a comparison diagram of the titer of the K1 group, the K2 group, the K3 group, and the K4 group lentivirus vectors after lyophilization according to Embodiment 4.
Figure 9:
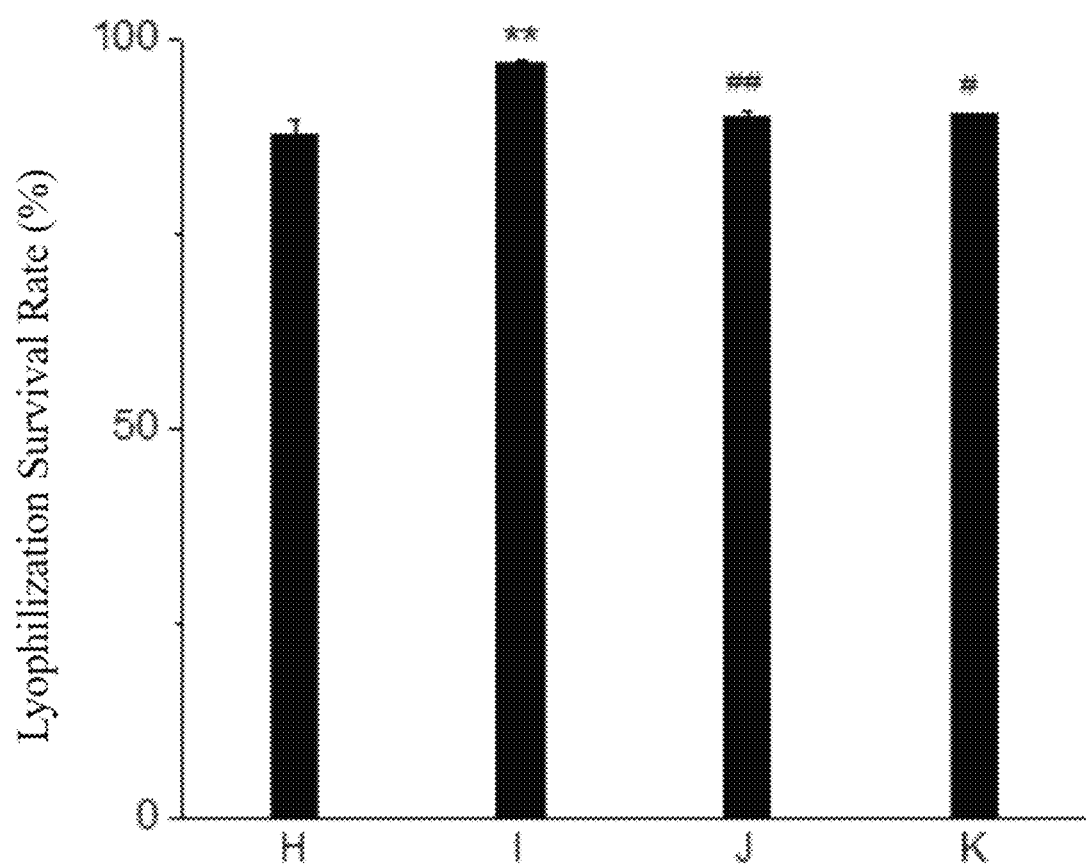
FIG. 9 is a comparison diagram of lyophilization survival rate of the K1 group, the K2 group, the K3 group, and the K4 group according to Embodiment 4.

Lyophilization survival rate=(virus titer after lyophilization/virus titer before lyophilization)×100%. The average titers of each group of lentiviral vectors before and after lyophilization are shown in Table 9. FIG. 8 shows the comparison of bio-titers of the lentiviral vectors after lyophilization in the K1, K2, K3, and K4 groups, wherein H stands for the K1 group, I stands for the K2 group, J stands for the K3 group, and K stands for the K4 group. * indicates that data compared with K1 group, **P<0.01 indicates statistical significance; # indicates that data compared with K2 group, #P<0.05, ##P<0.01 indicates statistical significance. The comparison of lyophilization survival rate of K1 group, K2 group, K3 group, and K4 group is shown in FIG. 9, wherein H stands for K1 group, I stands for K2 group, J stands for K3 group, K stands for K4 group. * indicates data compared with K1 group, **P<0.01 indicates statistical significance; # indicates that data compared with K2 group, #P<0.05, ##P<0.01 indicates statistical significance.

TABLE 9

Average Titers Of Each Group of Lentiviral Vectors Before and After Lyophilization

| Groups | Average Titers (TU/mL) | |
|---|---|---|
| | Before Lyophilization | After Lyophilization |
| K1 | $3.43 \times 10^7$ | $3.01 \times 10^7$ |
| K2 | $3.55 \times 10^7$ | $3.44 \times 10^7$ |
| K3 | $3.21 \times 10^7$ | $2.90 \times 10^7$ |
| K4 | $3.38 \times 10^7$ | $3.04 \times 10^7$ |
| Control | $4.21 \times 10^7$ | 0 |

As can be seen from FIG. 8 and FIG. 9, the bio-titer and lyophilization survival rate of the K2 group are greater than those of the K1, K3, and K4 groups. That indicates that compared with the K1, K3, and K4 groups, the protective agent in the K2 group can effectively reduce the damage of the lentiviral vector during the lyophilization process.

2. The appearance and resolubility (redispersion time) of lyophilization lentiviral vector preparations are shown in Table 10.

TABLE 10

Appearance and Resolubility (Redispersion Time) of Lyophilization Lentiviral Vector Preparations

| Groups | Appearance | Redispersion Time |
|---|---|---|
| K1 | Loose, Honeycomb | Good, Within 30 s |
| K2 | Loose, Honeycomb | Good, Within 30 s |
| K3 | Loose, Honeycomb | Good, Within 30 s |
| K4 | Loose, Honeycomb | Good, Within 30 s |

It can be seen from Table 10 that the lyophilization lentiviral vector preparations of K1, K2, K3, and K4 groups have the same shape, the state is good after reconstituting with water, and the redispersion time is within 30 s.

3. Stability of lyophilization lentiviral vector preparations

Lyophilization lentiviral vector preparations were stored at −20° C. for 3 months, 23° C. for 20 days, and 4° C. for 30 days respectively. Appearance, resolubility (redispersion Time), and bio-titer were tested after being stored. Titer recovery rate=(viral titer of Lyophilization lentiviral vector preparations after being stored for a period of time/viral titer before lyophilization)×100%.

It was observed that after being stored at −20° C. for 3 months, at 23° C. for 20 days, and at 4° C. for 30 days respectively, the appearance and resolubility of lyophilization lentiviral vector preparations of the K1, K2, K3, and K4 groups were good.

Figure 10:
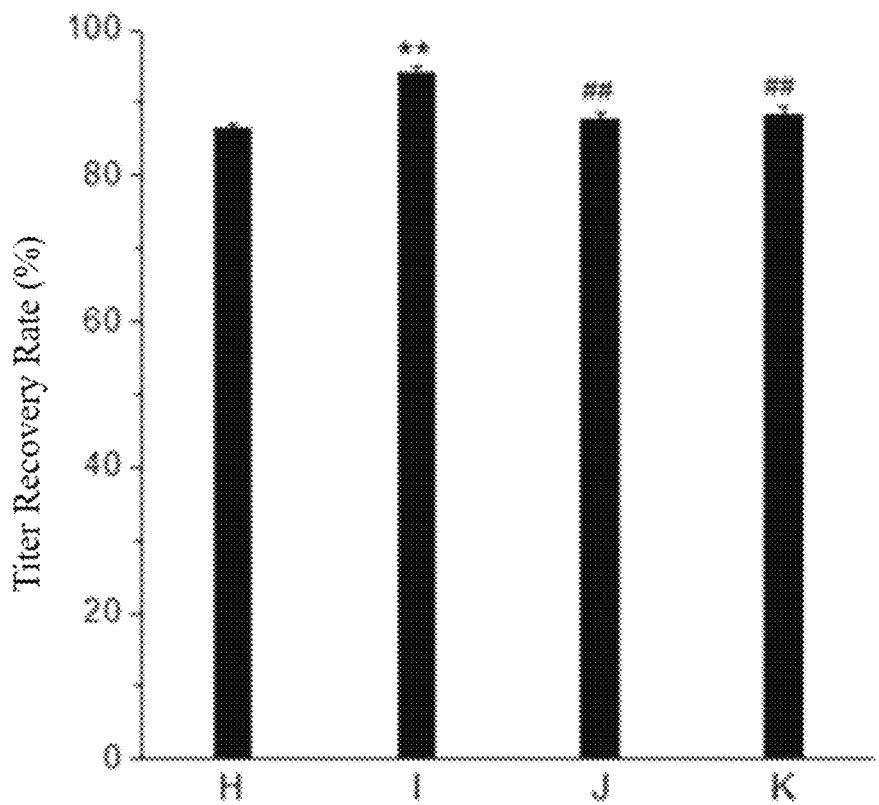
FIG. 10 is the titer recovery rate of the lentivirus vectors stored at −20° C. for 3 months according to Embodiment 4.
Figure 11:
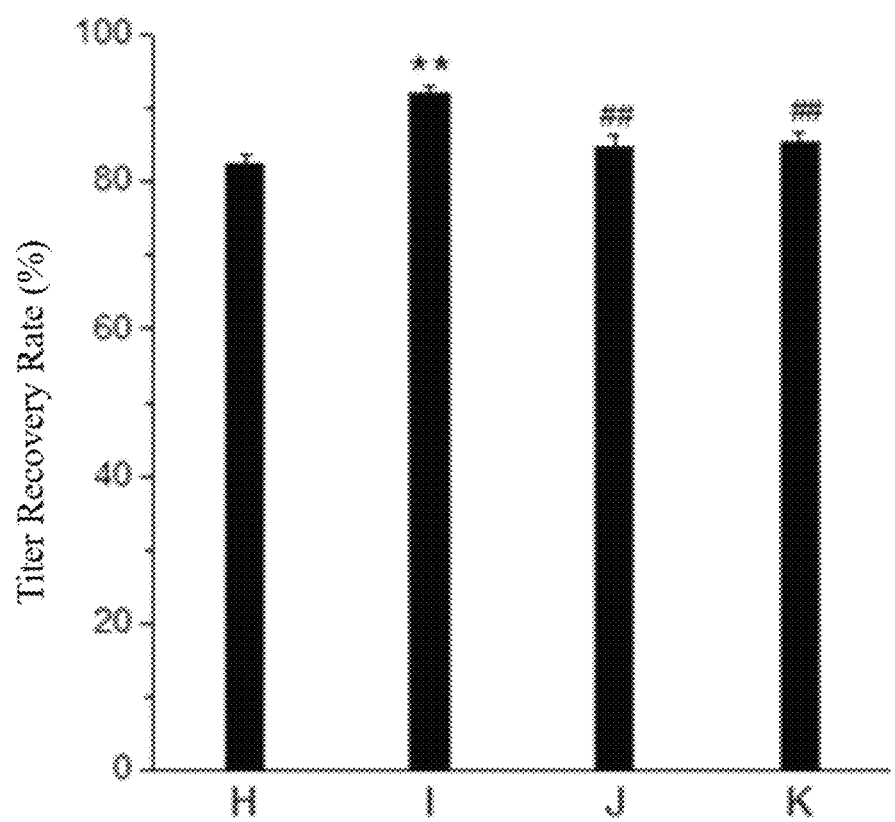
FIG. 11 is the titer recovery rate of the lentivirus vectors stored at 23° C. for 20 days according to Embodiment 4.

The titer recovery rates of lentiviral vectors stored at −20° C. for 3 months are shown in FIG. 10, wherein H stands for the K1 group, I stands for the K2 group, J stands for the K3 group, and K stands for the K4 group. * means compared with the K1 group, **P<0.01 indicates statistical significance; # indicates that data compared with K2 group, ##P<0.01 indicates statistical significance. The titer recovery rates of lentiviral vectors stored at 23° C. for 20 days is shown in FIG. 11, wherein H stands for the K1 group, I stands for the K2 group, J stands for the K3 group, and K stands for the K4 group, * means compared with the K1 group, **P<0.01 indicates statistical significance; # indicates that data compared with K2 group, ##P<0.01 indicates statistical significance. The titer recovery rate of lentiviral vectors stored at 4° C. for 30 days is shown in FIG. 12, wherein H stands for the K1 group, I stands for the K2 group, J stands for the K3 group, and K stands for the K4 group, * means compared with the K1 group, **P<0.01 indicates statistical significance; # indicates that data compared with K2 group, ##P<0.01 indicates statistical significance.

Figure 12:
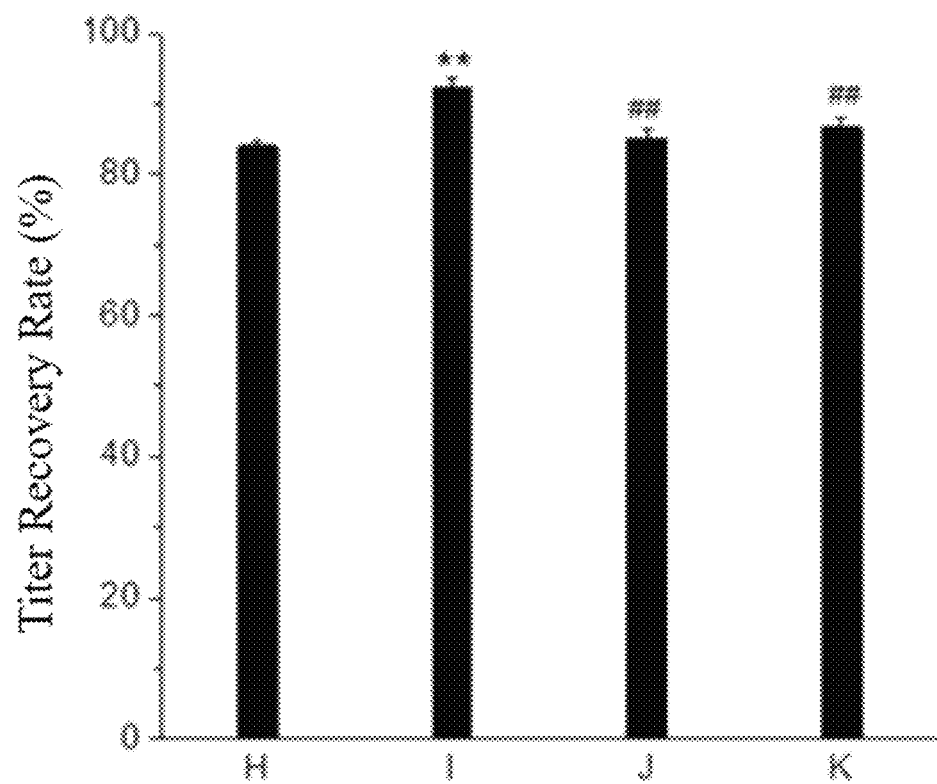
FIG. 12 is the titer recovery rate of the lentivirus vectors stored at 4° C. for 30 days according to Embodiment 4.

It can be seen from FIG. 10, FIG. 11, and FIG. 12 that the titer recovery rate of the lyophilization lentiviral vectors prepared in the K2 group stored at −20° C. for 3 months was 94.2%, which was greater than that of the K1 group, K3 group, and K4 group. The titer recovery rate of the lyophilization lentiviral vectors prepared in the K2 group stored at 23° C. for 20 days was 92.1%, which was greater than that of the K1 group, K3 group, and K4 group. The titer recovery rate of the lyophilization lentiviral vectors prepared in the K2 group stored at 4° C. for 30 days was 92.4%, which was greater than that of K1, K3, and K4 groups. That indicates that compared with K1, K3, and K4 groups, the Lyophilization lentiviral vector protective agent in K2 group can effectively reduce the loss and destruction of lentiviral titers during long-term storage. The inventor has analyzed how the lyophilization lentiviral vectors can protective agent in K2 group that can effectively reduce the loss and destruction of lentiviral titers during long-term storage. It may because the hydroxyl group on trehalose replaces the water molecule to partially bind to the protein surface. Due to glycerophosphorylcholine and diacetin being small molecules, they can enter the gap between the surface of protein and water molecules, and fill this gap through the entanglement of flexible molecular chains. In this way, the contact between the protein and the water molecule is reduced, thereby reducing the impact of ice crystals on the surface of the protein. The mechanical damage caused by lyophilization can also be reduced.

The conventional technology in the above-mentioned embodiments is the prior art known to those skilled in the art, so it will not be described in detail here.

The above embodiments are only used to illustrate the present invention, but not to limit the present invention. Those skilled in the art can also make various changes and modifications without departing from the spirit and scope of the present invention. Therefore, all equivalent technical solutions also belong to the scope of the present invention, and the patent protection scope of the present invention should be defined by the claims.

We claim:

1. A short hairpin RNA (shRNA) for inhibiting non-coding RNA SNHG17 expression, wherein the coding sequence of the shRNA is represented by any one of SEQ ID NO. 1, SEQ ID NO. 2, SEQ ID NO. 3 and SEQ ID NO. 4.

2. A composition comprising shRNA and fulvestrant, wherein the coding sequence of the shRNA is represented by any one of SEQ ID NO. 1, SEQ ID NO. 2, SEQ ID NO. 3 and SEQ ID NO. 4.

* * * * *

SEQUENCE LISTING

```
Sequence total quantity: 13
SEQ ID NO: 1            moltype = DNA  length = 63
FEATURE                 Location/Qualifiers
source                  1..63
                        mol_type = other DNA
                        organism = synthetic construct
SEQUENCE: 1
ccggtggatt gtcagctgac ctctgtttca agagaacaga ggtcagctga caatcctttt   60
ttg                                                                 63

SEQ ID NO: 2            moltype = DNA  length = 63
FEATURE                 Location/Qualifiers
source                  1..63
                        mol_type = other DNA
                        organism = synthetic construct
SEQUENCE: 2
```

```
aattcaaaaa aggattgtca gctgacctct gttctcttga acagaggtc agctgacaat    60
cca                                                                 63

SEQ ID NO: 3           moltype = DNA  length = 63
FEATURE                Location/Qualifiers
source                 1..63
                       mol_type = other DNA
                       organism = synthetic construct
SEQUENCE: 3
ccggtgtgac gtgtcttcaa gaagagttca agagactctt cttgaagaca cgtcactttt    60
ttg                                                                  63

SEQ ID NO: 4           moltype = DNA  length = 63
FEATURE                Location/Qualifiers
source                 1..63
                       mol_type = other DNA
                       organism = synthetic construct
SEQUENCE: 4
aattcaaaaa agtgacgtgt cttcaagaag agtctcttga actcttcttg aagacacgtc    60
aca                                                                  63

SEQ ID NO: 5           moltype = DNA  length = 20
FEATURE                Location/Qualifiers
source                 1..20
                       mol_type = other DNA
                       organism = synthetic construct
SEQUENCE: 5
tgcttgtaag gcagggtctc                                                20

SEQ ID NO: 6           moltype = DNA  length = 20
FEATURE                Location/Qualifiers
source                 1..20
                       mol_type = other DNA
                       organism = synthetic construct
SEQUENCE: 6
acagccactg aaagcatgtg                                                20

SEQ ID NO: 7           moltype = DNA  length = 29
FEATURE                Location/Qualifiers
source                 1..29
                       mol_type = other DNA
                       organism = synthetic construct
SEQUENCE: 7
agtctcccat gtctggaccc cgaatcttg                                      29

SEQ ID NO: 8           moltype = DNA  length = 20
FEATURE                Location/Qualifiers
source                 1..20
                       mol_type = other DNA
                       organism = synthetic construct
SEQUENCE: 8
tgttgtggat ctgacctgcc                                                20

SEQ ID NO: 9           moltype = DNA  length = 20
FEATURE                Location/Qualifiers
source                 1..20
                       mol_type = other DNA
                       organism = synthetic construct
SEQUENCE: 9
aagtcgcagg agacaacctg                                                20

SEQ ID NO: 10          moltype = DNA  length = 30
FEATURE                Location/Qualifiers
source                 1..30
                       mol_type = other DNA
                       organism = synthetic construct
SEQUENCE: 10
aggagctagc tgcttgtaag gcagggtctc                                     30

SEQ ID NO: 11          moltype = DNA  length = 30
FEATURE                Location/Qualifiers
source                 1..30
                       mol_type = other DNA
                       organism = synthetic construct
SEQUENCE: 11
aggagctagc tgcttgtaag gcagggtctc                                     30

SEQ ID NO: 12          moltype = DNA  length = 21
FEATURE                Location/Qualifiers
```

```
source                  1..21
                        mol_type = other DNA
                        organism = synthetic construct
SEQUENCE: 12
ggattgtcag ctgacctctg t                                              21

SEQ ID NO: 13           moltype = DNA  length = 21
FEATURE                 Location/Qualifiers
source                  1..21
                        mol_type = other DNA
                        organism = synthetic construct
SEQUENCE: 13
gtgacgtgtc ttcaagaaga g                                              21
```